(12) United States Patent
Allinquant et al.

(10) Patent No.: US 7,115,380 B2
(45) Date of Patent: Oct. 3, 2006

(54) APPLICATIONS OF PEPTIDES DERIVED FROM THE CYTOPLASMIC DOMAIN OF AMYLOID PRECURSOR PROTEIN (APP)

(75) Inventors: Bernadette Allinquant, Paris (FR); Alain Prochiantz, Paris (FR)

(73) Assignee: Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 11/118,429

(22) Filed: May 2, 2005

(65) Prior Publication Data

US 2005/0272658 A1    Dec. 8, 2005

Related U.S. Application Data

(62) Division of application No. 10/048,209, filed as application No. PCT/FR00/02174 on Jul. 28, 2000, now Pat. No. 6,905,832.

(30) Foreign Application Priority Data

Jul. 30, 1999   (FR) ................................. 99 09929

(51) Int. Cl.
*G01N 33/53* (2006.01)
*C07K 14/47* (2006.01)

(52) U.S. Cl. ............................. 435/7.1; 435/6; 530/324
(58) Field of Classification Search ................ None
See application file for complete search history.

(56) References Cited

U.S. PATENT DOCUMENTS 5,652,092 A   7/1997   Vitek et al. ............... 435/4
5,656,477 A   8/1997   Vitek et al. ............... 435/325
5,703,209 A  12/1997   Vitek et al. ............... 530/350
6,080,724 A   6/2000   Chassaing et al. .......... 514/13

FOREIGN PATENT DOCUMENTS

| WO | WO 93/07296 | 4/1993 |
| WO | WO 94/28412 | 12/1994 |
| WO | WO 98/28334 | 7/1998 |
| WO | WO 98/38861 | 9/1998 |

*Primary Examiner*—Robert A. Wax
(74) *Attorney, Agent, or Firm*—Morgan Lewis & Bockius LLP

(57) ABSTRACT

The invention concerns novel uses of peptides derived from the cytoplasmic domain of the amyloid protein precursor (APP); said peptides are in particular sequences including the membrane domain juxtaposed to the cytoplasmic domain of the amyloid protein precursor (APP) (one-letter code), selected in the group consisting of the sequences $Y_1$KQYTSIHHG$Y_0$ (SEQ ID NO:2). $Y_1$KKQYTSIHHG$Y_0$ (SEQ ID NO:3) and $Y_1$KKKQYTSIHHG$Y_0$ (SEQ ID NO:4), wherein $Y_0$ is nil or represents V, VV, VVE, VVEV or VVVED and $Y_1$ represents an internalisation and addressing peptide, derived from the 3rd helix of homeodomains and structually related peptides. The invention also concerns the use of a peptide comprising the membrane domain juxtaposed to the cytoplasmic domain of the amyloid protein precursor (APP), for selecting and screening products capable of inhibiting apoptosis.

2 Claims, 4 Drawing Sheets

Figure 1:
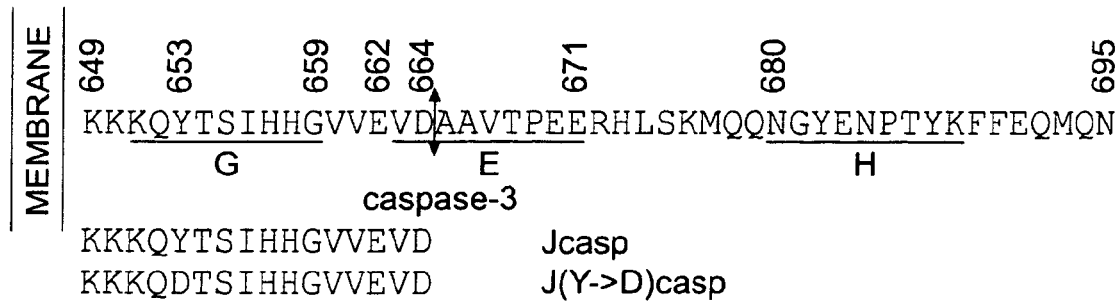

APPLICATIONS OF PEPTIDES DERIVED FROM THE CYTOPLASMIC DOMAIN OF AMYLOID PRECURSOR PROTEIN (APP)

This is a divisional of Ser. No. 10/048,209, filed Jun. 25, 2002, now U.S. Pat. No. 6,905,832, which is a 371 of PCT/FR00/02174, filed Jul. 28, 2000 which claims priority to French application 99/09929, filed Jul. 30, 1999.

The present invention relates to novel applications of peptides derived from the cytoplasmic domain of amyloid precursor protein (APP).

Amyloid precursor protein APP, is a protein of unknown function, the neuronal form of which comprises 695 amino acids; it has a single transmembrane domain (positions 625–648) and a short 47 amino acid cytoplasmic domain (positions 649–695) represented in the attached sequence listing under the number SEQ ID NO:1.

Alzheimer's disease is a neurodegenerative disorder which affects from 1 to 6% of the population over the age of 65. One of its characteristics is the presence of senile plaques which contain β-amyloid (βA4 or BAP), which is a toxic product derived from APP and consisting of peptides of 39 to 42 amino acids, which are engendered by cleavage of APP by two proteases, β- and γ-secretase. Moreover, a third enzyme, named α-secretase, cleaves APP between the β- and γ-sites, therefore making it impossible to form the supposedly pathogenic βA4. None of these secretases has, to date, been identified, even though there are legitimate suspicions regarding the PS1 protein (product of the Presenilin-1 gene, mutated in familial forms of Alzheimer's disease). In fact, PS1 may be either γ-secretase or one of its cofactors. Finally, other cleavage sites exist in the C-terminal domain, including the site for caspases (N. Barnes et al., J. Neuroscience, 1998, 18, 15, 5869–5880), between the aspartate and alanine residues of SEQ ID NO: 1 (positions 16 and 17). It remains that the mechanisms responsible for the toxicity of βA4 are unknown and that the relationship between the presence of βA4 in the plaques and the pathological condition has not been elucidated. It is probable that other factors and/or other domains of the molecule are also involved.

For this reason, many studies have tried to establish the physiological and/or physiopathological role of APP and of the various products of its metabolism. In fact, the physiological ligand, if it exists, of the N-terminal domain has not been identified and the signalling pathways are still poorly defined. One of the strategies for making it possible to analyze these signalling pathways is the identification of molecular partners of the cytoplasmic domain.

The cytoplasmic domain of APP, and also various peptides derived from this cytoplasmic domain, have in particular been studied:

the sequences YTSI, KKKQYTSIHHGVVEV (SEQ ID NO: 8), GYENPTY (SEQ ID NO: 9) and NPTY have been identified as internalization signals; more precisely, they are considered to be sequences for transcytosis of APP between the basolateral and apical compartments of MDCK epithelial cells (Haass et al., J. Cell Biol., 1995, 128, 4, 537–547; Lai et al., J. Biol. Chem., 1995, 270, 8, 3565–3573; Lai et al., J. Biol. Chem., 1998, 273, 6, 3732–3739);

the C-terminal cytoplasmic domain (APP-Cter) has been identified as:

being involved in regulating the GTPase activity of the αo subunit of heterotrimeric G protein (Brouillet et al., J. Neuroscience, 1999, 19, 5, 1717–1727);

interacting with several proteins: Pat-1 interacts with the juxtamembrane domain (KKKQYTSIHHG) and with the complete C-terminal domain and is thought to be involved in transporting APP along microtubules, toward the cell surface (Zheng et al., PNAS, 1998, 95, 14745–14750); the αo subunit of heterotrimeric G protein interacts with the median region of said C-terminal cytoplasmic domain, at the histidine doublet (HH)⁻(Nishimoto et al., Nature, 1993, 362, 75–79) and the Fe65 protein with the most distal region of the APP-Cter domain (Fiore et al., J. Biol. Chem., 1995, 270, 52, 30853–30856).

These various results show the complexity of the mechanisms in which amyloid precursor protein (APP) is involved.

The inventors have now shown that, surprisingly, peptides comprising the juxtamembrane domain (positions 649–664) of the cytoplasmic domain of amyloid precursor protein (APP) have, after internalization into cells, apoptotic activity.

A subject of the present invention is peptides, charcterized in that they consist of sequences which include the juxtamembrane domain of the cytoplasmic domain of amyloid precursor protein (APP) (one-letter code), and which are selected from the group consisting of the sequences $Y_1KQYTSIHHGY_0$ (SEQ ID NO: 2), $Y_1KKQYTSIHHGY_0$ (SEQ ID NO: 3) and $Y_1KKKQYTSIHHGY_0$ (SEQ ID NO: 4), in which $Y_0$ is null or represents V, VV, VVE VVEV or VVEVD and $Y_1$ represents an internalization and addressing peptide derived from the 3rd helix of homeodomains, and from structurally related peptides, and preferably corresponds to the sequence $X_1X_2X_3X_4X_5X_6X_7X_8X_9X_{10}X_{11}X_{12}X_{13}X_{14}X_{15}X_{16}$, in which $X_1$, $X_2$, $X_3$, $X_4$, $X_5$, $X_6$, $X_7$, $X_8$, $X_9$, $X_{10}X_{11}X_{12}X_{13}X_{14}$, $X_{15}$ and $X_{16}$ each represent an α-amino acid, 6 to 10 of said amino acids being hydrophobic and $X_6$ representing a tryptophan.

Among the preferred $Y_1$ sequences, mention may be made of the sequence KQIKIWFQNRRMKWKK (SEQ ID NO: 5).

The peptides $X_1X_2X_3X_4X_5X_6X_7X_8X_9X_{10}X_{11}X_{12}X_{13}X_{14}X_{15}X_{16}$ have in particular been described in International Application WO 97/12912.

The peptides according to the invention cause apoptosis of the cells into which they are internalized and may advantageously be used to select and screen products capable of inhibiting cellular apoptosis.

Another subject of the present invention is therefore also the use of a peptide comprising the juxtamembrane domain of the cytoplasmic domain of amyloid precursor protein (APP), for selecting and screening products capable of inhibiting apoptosis.

According to an advantageous embodiment of said use, the peptide comprising the juxtamembrane domain of the cytoplasmic domain of amyloid precursor protein (APP) is combined with an internalization peptide selected from the group consisting of peptides capable of crossing the blood-brain barrier.

By way of examples of internalization peptides which can be used in the present invention, mention may be made of:

internalization and addressing peptides derived from the 3rd helix of homeodomains and peptides structurally related to the latter, peptides derived from viral proteins: VP22 (G. Elliott et al., Cell, 1997, 88, 223–233; A. Prochiantz, Current Opinion in Cell Biology, 2000, 12, 399–406); peptides derived from the HIV Tat protein transduction domain (Schwarze S R et al., Science, 1999, 285, 5433, 1569–1572), and also other peptides, such as those described in A. Prochiantz, 2000, mentioned above; M. Lindgren et al., TIPS, 2000, 21, 99–103 or C. Rousselle et al., Mol. Pharmacol., 2000, 57, 679–686 (amphiphilic peptides, peptides derived from signal sequences, transportan, etc.).

Preferably, the peptide used in the present invention is selected from the group consisting of the sequences (one-letter code) $Y_1$KQYTSIHHGY$_0$ (SEQ ID NO: 2), $Y_1$KKQYTSIHHGY$_0$ (SEQ ID NO: 3) and $Y_1$KKKQYTSIHHGY$_0$ (SEQ ID NO: 4), in which $Y_0$ is null or represents V, VV, VVE VVEV or VVEVD and $Y_1$ is null or represents an internalization and addressing peptide derived from the 3rd helix of homeodomains, and from structurally related peptides, and preferably corresponds to the sequence $X_1X_2X_3X_4X_5X_6X_7X_8X_9X_{10}X_{11}X_{12}X_{13}X_{14}X_{15}X_{16}$, in which $X_1$, $X_2$, $X_3$, $X_4$, $X_5$, $X_6,X_7X_8X_9X_{10}X_{11}X_{12}X_{13}X_{14}$, $X_{15}$ and $X_{16}$ each represent an α-amino acid, 6, to 10, of said amino acids being hydrophobic and $X_6$, representing a tryptophan.

The peptide of SEQ ID NO: 2, in which $Y_1$, is null and $Y_0$ is null is named peptide G (see also FIG. 1).

The peptide of SEQ ID No. 4, in which $Y_1$, is null and $Y_0$ represents VVEVD is named Jcasp (or Gcasp).

Another subject of the present invention is also the use of cells, into which a peptide as defined above has been internalized, for selecting and screening products capable of inhibiting apoptosis.

Another subject of the present invention is also a method for screening and selecting products capable of inhibiting apoptosis, characterized in that it comprises:
bringing the potential inhibitor into contact with a cell into which a peptide as defined above has been internalized, and
measuring cleavage of DNA (revealed in particular by TUNEL labeling) or of actin (revealed, for example, with an anti-fractin antibody) or measuring the p20 subunit of caspase 3, (for example by specific labeling).

Another subject of the present invention is also the use of a peptide as defined above, for preparing an anticancer medicinal product.

Another subject of the present invention is also peptides, characterized in that they are selected from the group consisting of the sequences (one-letter code) $Y_1$KQYTSIHHGY$_0$, (SEQ ID NO: 2, ) and $Y_1$KKQYTSIHHGY$_0$, (SEQ ID NO: 3, ), in which $Y_0$, is null or represents V, VV, VVE VVEV or VVEVD and $Y_1$, is null, and of the peptide of formula $Y_1$KKKQYTSIHHGY$_0$, (SEQ ID NO: 4, ), in which $Y_0$ represents VVEVD and $Y_1$, is null.

Figure 2:
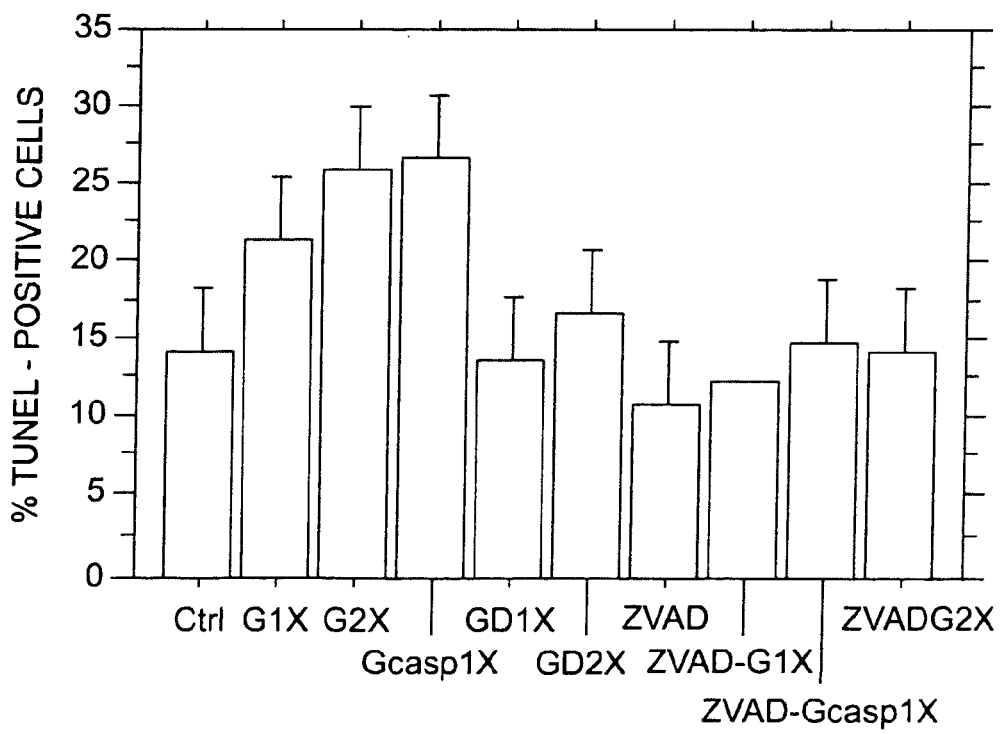
Figure 3:
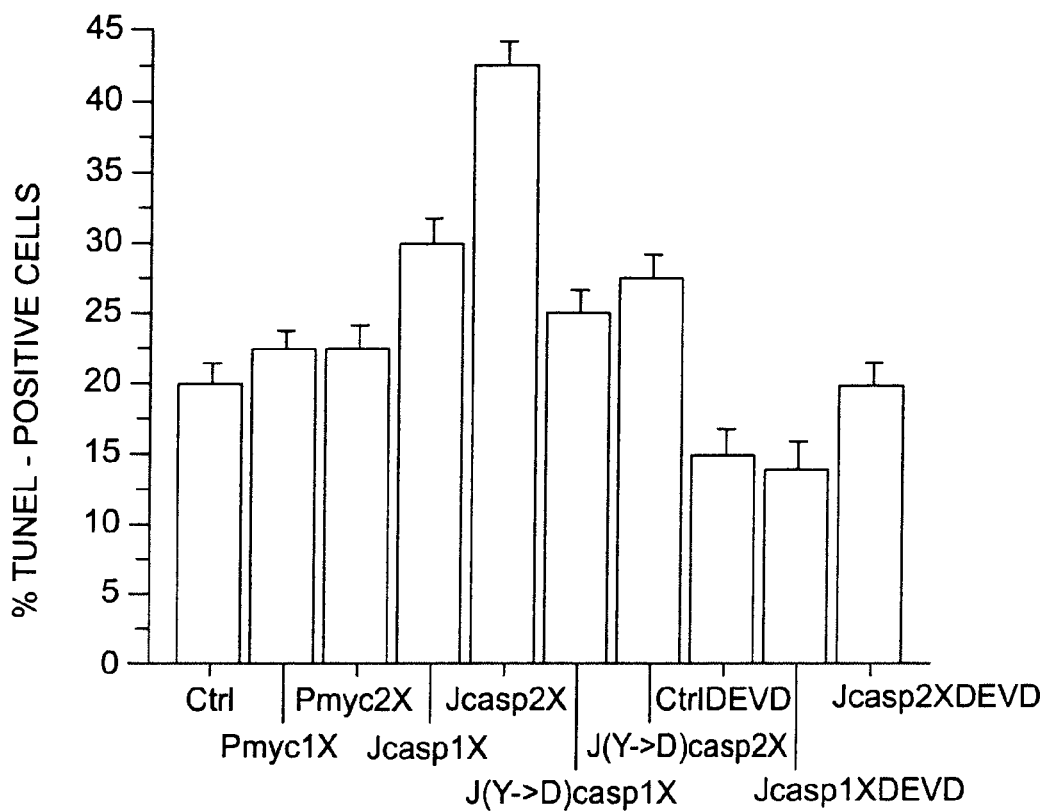
Figure 4:
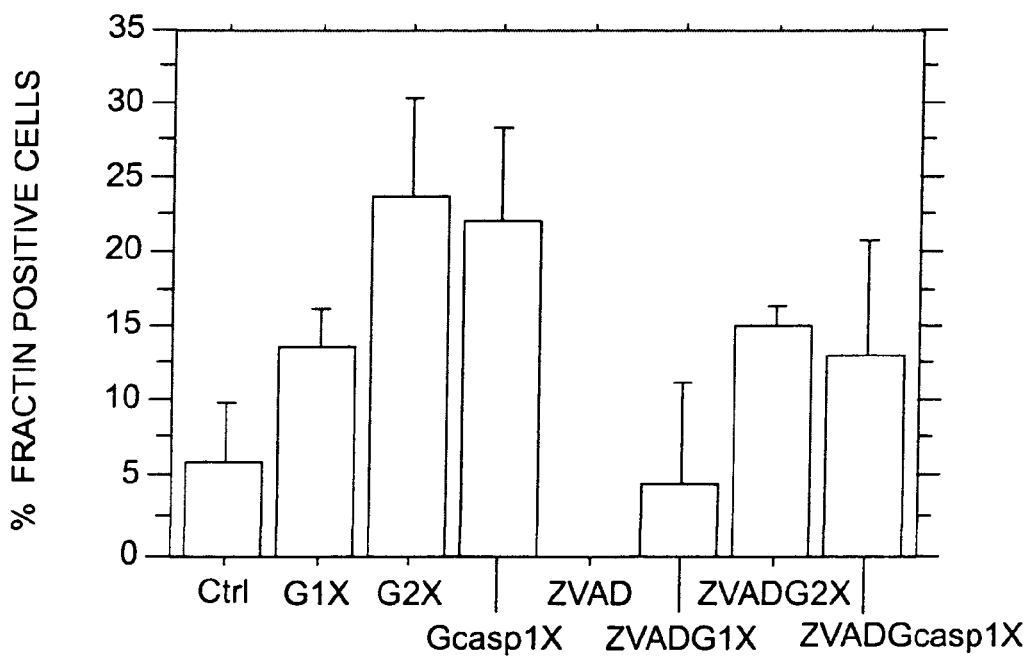
Figure 5:
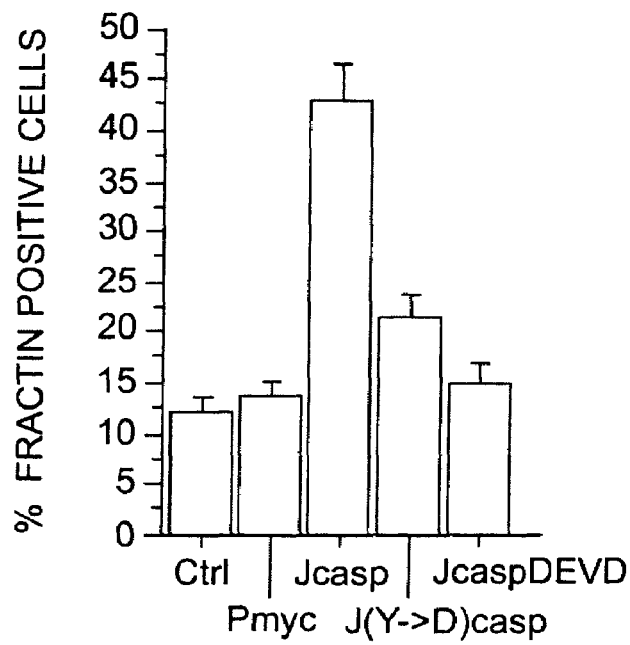
Figure 6:
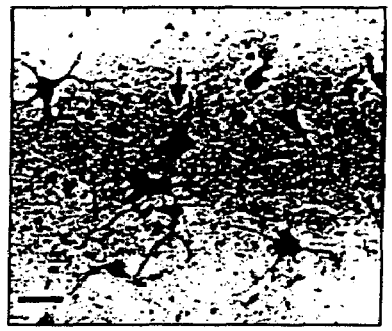
Figure 7:
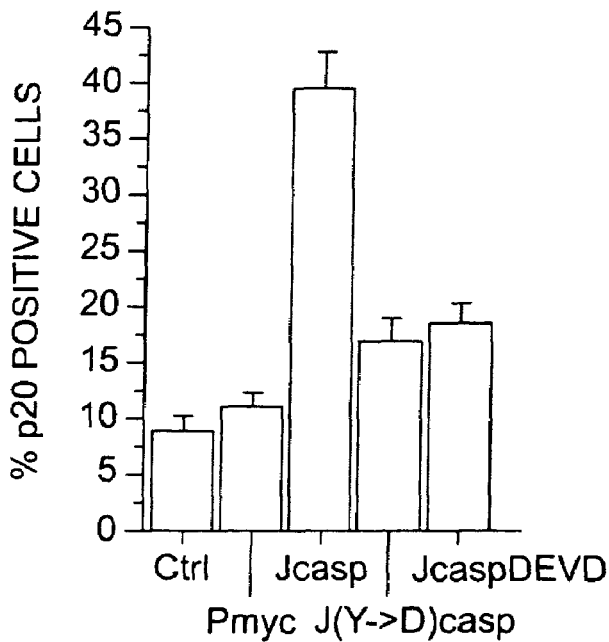
Figure 8A:
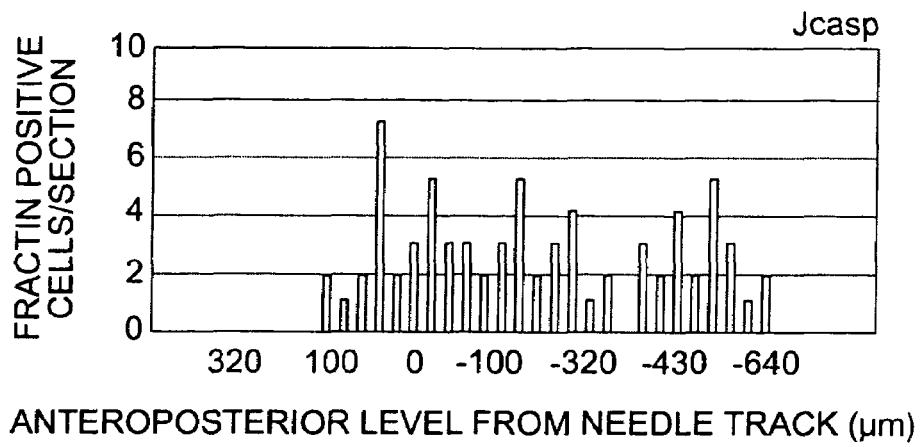
Figure 8B:
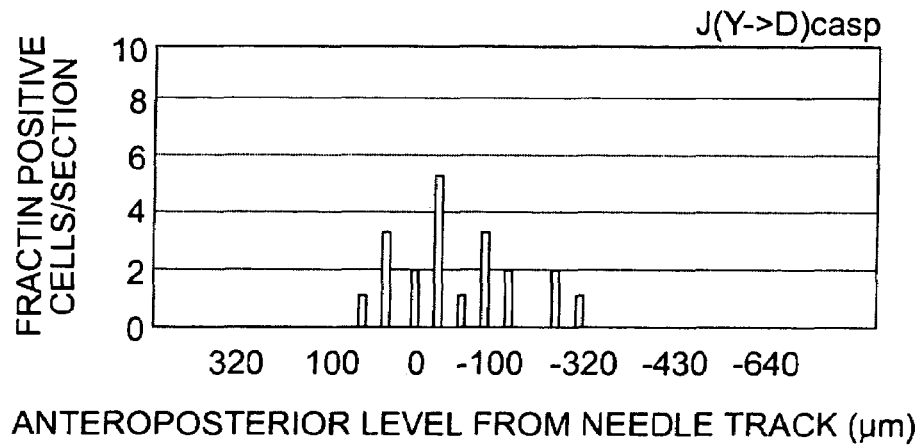
Figure 8C:
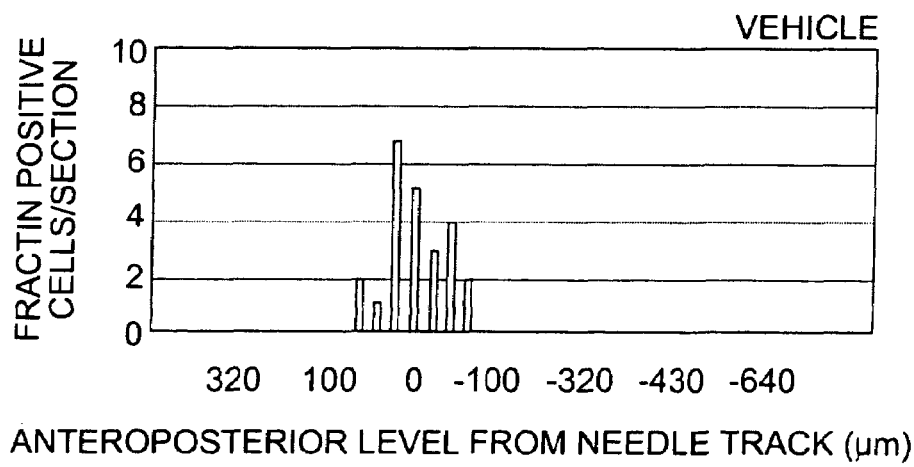

The invention will be more clearly understood by virtue of the attached figures in which:

FIG. 1 represents the sequence of the cytoplasmic domain of amyloid precursor protein (APP): positions 649–695, , and also some of its fragments: peptide G: positions 651–659; peptide E: positions 663–671; peptide H; positions 680–688; peptide Jcasp: positions 649–664, FIGS. 2 and 3 represent the quantification of the cleavage of DNA using the TUNEL technique, 24, h after internalization of the peptides, FIGS. 4 and 5 represent the quantification of the cleavage of actin by caspase 3, using an anti-fractin antibody, FIG. 6 illustrates detection of p20, in a neuron by immunolabeling (arrow) (alkaline phosphatase); the p20 is present in all compartments; scale: 10 μm, FIG. 7 illustrates activation of p20 by peptide Jcasp (2.4 μM), FIG. 8 illustrates the results obtained in vivo: representative diagrams (one experiment, one animal per condition) of the distribution of fractin-positive cells in adjacent sections. The value 0 is arbitrarily attributed to the site of injection. The peptide Jcasp shows a greater number of fractin-positive cells compared to peptide J(Y→D)casp or to the control.

EXAMPLE 1

Materials and Methods 1.1 Primary Cultures of Neurons

Cortical and corticostriatal neurons are prepared, as described previously (Lafont et al., Development, 1992, 114, 17–29, ), from E14, mouse embryos or from E15, rat embryos.

Briefly, the dissociated cells are plated out onto polyornithine-coated plastic plates (ELISA-type plates) at a density of 5,000, cells per well, and incubated in a suitable medium supplemented with hormones, proteins and salts.

In order to verify the internalization of the peptide studied, the cells are plated out onto polyornithine-coated glass slides at a density of 100,000, cells per slide.

1.2, Preparation of Peptides

The V1, vector (Penetratin or P=KQIKIWFQNRRMKWKK) (SEQ ID NO: 5) is used as an internalization peptide which, after genetic or chemical fusion to a cargo, allows the translocation thereof across the plasma membrane and the cytoplasmic and nuclear addressing thereof.

Several peptides were thus prepared:
SEQ ID NO: 5+ entire cytoplasmic domain of APP (SEQ ID NO: 1).
$Y_1$KKKQYTSIHHGY$_0$: SEQ ID NO: 4 in which $Y_0$ is null or represents VVEVD (Jcasp) and $Y_1$ represents SEQ ID NO: 5; the portion in bold corresponds to peptide G of FIG. 1.
$Y_1$KQYTSIHHGY$_0$: SEQ ID NO: 2 in which $Y_0$ is null (peptide G) and $Y_1$ represents SEQ ID NO: 5; the portion in bold corresponds to peptide G of FIG. 1.
$Y_1$KKQYTSIHHGY$_0$: SEQ ID No. 3 in which $Y_0$ is null and $Y_1$ represents SEQ ID No. 5; the portion in bold corresponds to peptide G of FIG. 1.
SEQ ID NO: 5+ domain E (VDAAVTPEE, SEQ ID NO: 6), underlined in the sequence according to FIG. 1.
SEQ ID NO: 5+ domain H (NGYENPTYK, SEQ ID NO: 7), underlined in the sequence according to FIG. 1.
SEQ ID NO: 5+ peptide corresponding to the MYC sequence [EQKLISEED] (Pmyc peptide).
SEQ ID NO: 5+ peptide J(Y→D)casp.

Peptide G corresponds to a transcytosis signal and comprises a tyrosine residue (Y); the peptide was also internalized either after phosphorylation of this tyrosine (Y-P) or after its substitution with an alanine (Y→A) or an aspartate (Y→D). The two substitutions totally abolish the physiological effects of G, whereas phosphorylation reduces them without abolishing them. In so far as Y→D mimics a phosphorylation, it may be proposed, as a parcimonious hypothesis, that the tyrosine is necessary, but that the phosphorylation thereof probably is not, the intermediate effect of Y-P possibly then being explained by dephosphorylation of the peptide in the cell. It cannot, however, be excluded that phosphorylation is necessary but that the substitution Y→D is not sufficient to mimic it.

These various peptides are synthesized chemically (95–98% purity, Synthem, France) with (Jcasp and J(Y→D)casp) or without N-terminal biotin and an aminopentanoic acid spacer arm (Derossi et al., J. Biol. Chem., 1994, 269, 10444–10450).

It should be noted that, since the last 2 amino acids of the sequence SEQ ID NO: 5 are lysines (KK), peptide G (KQYTSIHHG) is artificially extended by 2 amino acids.

1.3 Internalization of the Recombinant Peptides into Neurons

The internalization conditions are the same as those described in International Application WO 97/12912.

All the peptides are added to the cells two hours after the latter have been plated out. The internalization is verified by confocal microscopy after immunolabeling (Pmyc) or detection of biotin (Jcasp and its variants).

The internalization and the intracellular stability of Jcasp, Pmyc and J(Y→D)Casp are identical. The irreversible caspase inhibitors zVAD-fmk (100 µM) and zDEVD-fmk (200 µM) (Calbiochem, France) are added 1 hour before addition of the peptide.

1.4 Immunocytochemistry and Quantification of Apoptotic Cells

The apoptotic cells are detected by TUNEL labeling (fluorescein or alkaline phosphatase kits) as described by the supplier (Roche Diagnostics, France).

For the immunodetection of the fractin or of the p20 subunit of caspase 3 (Pharmingen), the cells are fixed with 4% paraformaldehyde (30 minutes, room temperature), washed three times with PBS and saturated for 1 hour at 37° C. with 10% fetal calf serum (FCS) in PBS containing 0.2% of Triton X 100.

Purified primary antibodies directed against fractin or p20 are diluted (in PBS-FCS) 2000-fold and 500-fold, respectively, incubated overnight at 4° C. washed three times and incubated with biotinylated anti-rabbit antibodies.

The detection is carried out using the alkaline phosphatase amplification kit (Vector, France).

For each condition, 600 to 800 cells are counted three times.

The statistical analysis is carried out with ANOVA and the Scheffé test.

1.5 In vivo Tests

1 µl (0.2 µl/min) of 2.7 µM of Jcasp (n=8) or J(Y→D) Casp (n=6), or of PBS (n=3) is injected stereotactically into the cortex of adult mice with the co-ordinates A=0, L=2 and D=1.5 (mouse brain Atlas by KBJ Franklin and G. Paxinos, Academic Press). 24 hours later, the animals are sacrificed and perfused with 4% paraformaldehyde, and the brains are extracted and cryoprotected.

Frozen sections (16 µm thick) are prepared and used for TUNEL detection or detection by fractin immunocytochemistry, using the purified primary antibody (1/100th dilution in PBS-FCS) without amplification and an anti-rabbit secondary antibody labeled with Cy3 and diluted to 1/400th (Jackson Immunoresearch Laboratories, Inc.). The number of fractin-positive cells is counted on adjacent sections. The statistical analysis is carried out by ANOVA and the Fischer test.

EXAMPLE 2

In Vitro Results 2.1. Induction of Neuronal Apoptosis

Internalization of the entire C-ter domain (APP-Cter) is not toxic but has, however, a negative effect on neurite growth. The internalization of peptides E and H has no effect, whereas that of peptide G, at concentrations lower than one µM, reproduces the effects of the intact C-terminal domain.

The most advantageous result is that peptide G, at concentrations of the order of 1 to 1.5 µM, or peptide Jcasp, at concentrations of 1.2 to 2.4 µM, causes neuronal death, and that this death corresponds to an apoptotic, and therefore regulated, process.

The apoptotic nature of the death caused by the internalization of peptide G or of peptide Jcasp (FIGS. 2–7) is demonstrated by the DNA fragmentation, revealed by the "TUNEL" method (FIGS. 2 and 3), and by the activation of caspases (FIGS. 4–7). The activation of caspases is demonstrated by the appearance of cleaved forms of actin and by the blocking of apoptosis by caspase inhibitors with a broad spectrum of activity (inhibitor of caspase 1, 3, 4 and 7), such as zVAD or zDEVD-fmk (FIGS. 4, 5 and 7), more specific for caspase 3.

FIGS. 2 and 3 illustrate the quantification of the DNA cleavage by the TUNEL technique 24 h after internalization of the peptides.

Peptide G was internalized at 2 concentrations (1X and 2X) and peptide Gcasp (or Jcasp) was internalized at the 1X concentration, in the presence or absence of the caspase inhibitor zVAD.

Each condition was tested in triplicate. The percentage of positive cells was evaluated after 24 h by counting approximately 1000 cells per well. The graph indicates a significant increase in the DNA cleavage in the presence of peptide G alone (concentration 1X: $p<0.0001$; concentration 2X: $p<0.0001$) and of peptide Jcasp (or Gcasp) (KKKQYTSIHHGVVEVD) (SEQ ID NO. 4 in which $Y_0$=VVEVD and $Y_1$=SEQ ID NO: 5) (concentration 1X:$p<0.0001$). The ZVAD inhibits this increase in cleavage.

Peptide Jcasp induces neuronal apoptosis. Two hours after plating out onto plates, peptide Jcasp is added to the E15 rat cortical neurones and cell death is evaluated by the TUNEL effect, 24 hours later. FIG. 3 shows that peptide Jcasp (1.2 and 2.4 µM) produces DNA fragmentation.

Substitution of the tyrosine with an aspartate decreases cell death, as for peptide G, whereas the internalization of a myc peptide which has no relation to APP and is linked to penetratin (Pmyc) has no effect on the number of positive cells obtained by the TUNEL method.

Since the DNA fragmentation suggests apoptosis, the same experiment was carried out in the presence of zDEVD-fmk, which inhibits caspase 3. At 200 µM, ZDEVD-fmk has a weak effect on basal cell death and inhibits the DNA fragmentation induced by peptide Jcasp at 1.2 µM and 2.4 µM (FIG. 3).

Similar inhibitions are obtained with the inhibitor zVAD-fmk (100 µM), (see FIG. 2).

Peptide Jcasp not linked to penetratin (internalization sequence of SEQ ID NO: 5), which is therefore not internalized, does not induce any DNA fragmentation.

2.2. The Induction of Apoptosis is Linked to the Activation of Caspase 3

Quantification of the actin cleavage by caspase 3 using an anti-fractin antibody.

FIGS. 4 and 5 illustrate the quantification of the actin cleavage by caspase 3 using the anti-fractin antibody, by immunocytochemistry after fixing the cells with paraformaldehyde (F. Yang et al., Am. J. Pathol., 1998, 152, 2, 379–389). The anti-fractin antibody specifically recognizes actin cleaved by caspase 3. The percentage of fractin-positive neurons was determined after 24 h of internalization of the peptides, by counting approximately 1000 cells per well in triplicate. In the presence of peptides G (KQYTSIHHG=SEQ ID NO: 2 in which $Y_1$ represents an internalization and addressing peptide, as defined above, and $Y_0$ is null) (1X and 2X) and Gcasp (or Jcasp) (KKKQYTSIHHGVVEVD=SEQ ID NO: 4 in which $Y_1$ represents an internalization and addressing peptide, as defined above, and $Y_0$ represents VVEVD) (1X), there is a significant increase in the cleavage by actin (G1X: p<0.0003; G2X:p<0.0001; GcasplX:p<0.0001). The zVAD alone inhibits all endogenous cleavage, by caspases, of neurones and significantly inhibits the increase in this cleavage with G1X, G2X and Gcasp1X (G1X/zVADG1X: p<0.0001; G2X/zVADG2X: p<0.0001; Gcasp/zVADGcasp: p<0.0001), even though the inhibition is not complete.

FIG. 5 shows that peptide Jcasp induces actin cleavage. It also shows that peptide J(Y→D)casp is relatively inactive and that the inhibitor zDEVD-fmk, which is more specific for caspase 3, inhibits the actin cleavage induced by peptide Jcasp.

quantification of the actin cleavage by caspase 3 by measuring p20

In order to verify that caspase 3 is effectively involved in the apoptosis caused by peptide Jcasp, use is made of the fact that this enzyme (caspase 3) is synthesized in the form of a propetide (37 kDa) which, after stimulation, generates an active subunit of 17–22 kDa (p20).

Immunoreactivity for p20 is examined in mouse cortical embryonic neurons cultured for 24 hours in the presence of several peptides. FIG. 6 illustrates the immunoreactivity for the p20 protein and FIG. 7 quantifies the induction of the p20.

Peptide Jcasp (2.4 µM) induces maturation of p20; significantly less effect is obtained with peptide J(Y→D)casp, confirming the importance of the tyrosine residue in caspase 3 induction.

The inhibitor zDEVD-fmk significantly decreases the activation of p20, suggesting that the apoptosis induced by peptide Jcasp involves maturation of caspase 3.

The inventors have therefore clearly shown the pro-apoptotic nature of peptide G internalized by virtue of its linkage to vector V1.

Such a property is of interest for the following reasons:

1. The entire C-terminal domain is not pro-apoptotic.

2. There is a cleavage site for caspases between the aspartate (D) and alanine (A) residues marked in bold in the sequence of APP-Cter (FIG. 1).

It is therefore possible to put forward the hypothesis that the cleavage between D and A unmasks a sequence KKKQYTSIHHGVVEVD (=SEQ ID NO: 4, in which $Y_1$ is null and $Y_0$ represents VVEVD) with apoptotic activity. This is particularly important since it reveals a mechanism involved in the neuronal loss which accompanies dementias of the Alzheimer type.

The first advantage of having identified an APP-derived peptide corresponding to a domain, normally exposed after in vivo cleavage and capable of causing cells to enter into apoptosis is to propose an original mechanism which may shed light on certain aspects of Alzheimer pathology and therefore to discover novel therapeutic approaches (development of inhibitors).

Moreover, the linking of the G sequence to the V1 vector makes it possible to produce a peptide which, once internalized by neurons in culture, brings about their apoptosis. Because of the properties of V1, entry occurs in 100% of the cells, whatever their degree of maturation in vitro, and these cells are normal (primary cultures).

The aspartate at position 664 corresponds to the cleavage site for caspase; the peptide according to the invention, when it is internalized into neuronal cells, activates caspase 3, causes actin cleavage at a caspase-sensitive site and induces DNA fragmentation.

Surprisingly, the peptides in accordance with the invention which do not comprise BAP, thus have pro-apoptotic properties both in vitro and in vivo.

EXAMPLE 3

In Vivo Results

The in vitro results (see example 2) demonstrate that the internalization of Jcasp by mouse or rat cortical neurons causes apoptosis by activation of a caspase and suggest that caspase 3 is one of the caspases activated.

In order to verify whether peptide Jcasp is also active in vivo and in the adult brain, 1 µl of peptide Jcasp, of peptide J(Y→D)casp (each at 2.7 µM in a saline buffer) or of saline buffer is injected into the mouse cerebral cortex. 24 hours later, the number of fractin-positive cells is quantified on each side of the injection site.

FIG. 8 illustrates the results obtained. Although variations were observed between the various experiments, they all gave similar results showing a considerable and specific effect of peptide Jcasp on the number of fractin-positive cells (mean±SEM: Jcasp (8 animals), 40.7±10.9; J(Y→D)casp (6 animals), 13±3.2; control (3 animals): 8±8; Jcasp vs control: p<0.05; Jcasp vs J(Y→D)casp: p<0.04; control vs J(Y→D) casp:NS)

In vivo applications, with infusion of the peptide using mini pumps, are also possible.

On this basis, this system constitutes a rapid and simple test for screening libraries of products which act specifically on the apoptotic death induced by this peptide, and are inoffensive on other models of apoptosis.

The identification of such substances is therefore very useful for developing treatments for the apoptosis which accompanies Alzheimer's disease.

The invention claimed is:

1. A method of selecting and screening products capable of inhibiting apoptosis comprising detecting inhibition of the capacity of the juxtamembrane domain located between positions 649 and 664 of the cytoplasmic domain of amyloid precursor protein (SEQ ID No.: 1) to induce apototic activity subsequent to internalization into a cell.

2. The method of claim 1, wherein said peptide is combined with an internalization peptide selected from the group consisting of internalization peptides capable of crossing the blood-brain barrier.

* * * * *

SEQUENCE LISTING

<160> NUMBER OF SEQ ID NOS: 9

<210> SEQ ID NO 1
<211> LENGTH: 47
<212> TYPE: PRT
<213> ORGANISM: Homo sapiens

<400> SEQUENCE: 1

Lys Lys Lys Gln Tyr Thr Ser Ile His His Gly Val Glu Val Asp
1               5                   10                  15

Ala Ala Val Thr Pro Glu Glu Arg His Leu Ser Lys Met Gln Gln Asn
            20                  25                  30

Gly Tyr Glu Asn Pro Thr Tyr Lys Phe Phe Glu Gln Met Gln Asn
        35                  40                  45

<210> SEQ ID NO 2
<211> LENGTH: 9
<212> TYPE: PRT
<213> ORGANISM: Homo sapiens

<400> SEQUENCE: 2

Lys Gln Tyr Thr Ser Ile His His Gly
1               5

<210> SEQ ID NO 3
<211> LENGTH: 10
<212> TYPE: PRT
<213> ORGANISM: Homo sapiens

<400> SEQUENCE: 3

Lys Lys Gln Tyr Thr Ser Ile His His Gly
1               5                   10

<210> SEQ ID NO 4
<211> LENGTH: 11
<212> TYPE: PRT
<213> ORGANISM: Homo sapiens

<400> SEQUENCE: 4

Lys Lys Lys Gln Tyr Thr Ser Ile His His Gly
1               5                   10

<210> SEQ ID NO 5
<211> LENGTH: 16
<212> TYPE: PRT
<213> ORGANISM: Homo sapiens

<400> SEQUENCE: 5

Lys Gln Ile Lys Ile Trp Phe Gln Asn Arg Arg Met Lys Trp Lys Lys
1               5                   10                  15

<210> SEQ ID NO 6
<211> LENGTH: 9
<212> TYPE: PRT
<213> ORGANISM: Homo sapiens

<400> SEQUENCE: 6

Val Asp Ala Ala Val Thr Pro Glu Glu
1               5

<210> SEQ ID NO 7
<211> LENGTH: 9

-continued

```
<212> TYPE: PRT
<213> ORGANISM: Homo sapiens

<400> SEQUENCE: 7

Asn Gly Tyr Glu Asn Pro Thr Tyr Lys
 1               5

<210> SEQ ID NO 8
<211> LENGTH: 15
<212> TYPE: PRT
<213> ORGANISM: Homo sapiens

<400> SEQUENCE: 8

Lys Lys Lys Gln Tyr Thr Ser Ile His His Gly Val Val Glu Val
 1               5                   10                  15

<210> SEQ ID NO 9
<211> LENGTH: 7
<212> TYPE: PRT
<213> ORGANISM: Homo sapiens

<400> SEQUENCE: 9

Gly Tyr Glu Asn Pro Thr Tyr
 1               5
```